United States Patent
Oh et al.

(10) Patent No.: US 6,867,340 B2
(45) Date of Patent: Mar. 15, 2005

(54) DISPROPORTIONATION/TRANSALKYLATION OF AROMATIC HYDROCARBONS

(75) Inventors: Seung-Hoon Oh, Taejon (KR); Sang-Il Lee, Taejon (KR); Kyoung-Hak Seong, Taejon (KR); Sang-Hoon Park, Seoul (KR)

(73) Assignee: SK Corporation, Seoul (KR)

( * ) Notice: Subject to any disclaimer, the term of this patent is extended or adjusted under 35 U.S.C. 154(b) by 181 days.

(21) Appl. No.: 10/268,649

(22) Filed: Oct. 10, 2002

(65) Prior Publication Data

US 2003/0036670 A1 Feb. 20, 2003

Related U.S. Application Data

(63) Continuation of application No. 09/720,723, filed as application No. PCT/KR99/00619 on Oct. 14, 1999, now abandoned.

(30) Foreign Application Priority Data

Dec. 24, 1998 (KR) .............................................. 98-58628
Mar. 22, 1999 (KR) .............................................. 99-9649

(51) Int. Cl.$^7$ .......................................... C07C 15/08
(52) U.S. Cl. ...................................... 585/475; 585/467
(58) Field of Search .................................. 585/467, 475

(56) References Cited

U.S. PATENT DOCUMENTS

| | | | |
|---|---|---|---|
| 3,702,293 A | 11/1972 | Hayes et al. ................ 208/139 |
| 4,083,886 A | 4/1978 | Michalko | |
| 4,645,752 A | 2/1987 | Dufresne et al. ........... 502/154 |
| 4,723,048 A | 2/1988 | Dufresne et al. | |
| 4,939,110 A | 7/1990 | Sachtler et al. ............... 502/66 |
| 4,977,121 A | 12/1990 | Dufresne et al. ............. 502/66 |
| 5,030,787 A | 7/1991 | Absil et al. | |
| 5,416,052 A | 5/1995 | de Agudelo et al. .......... 502/74 |
| 5,475,179 A | 12/1995 | Shamshoum et al. | |
| 5,475,180 A | 12/1995 | Chang et al. | |
| 5,759,950 A | 6/1998 | Gui et al. .................... 502/325 |
| 5,804,059 A | 9/1998 | Wu et al. .................... 208/135 |
| 5,898,011 A | 4/1999 | Wu et al. .................... 502/327 |
| 6,060,417 A | 5/2000 | Kato et al. .................... 502/64 |
| 6,150,292 A | 11/2000 | Merlen et al. ................. 502/64 |
| 6,486,372 B1 | 11/2002 | Merlen et al. ............... 585/467 |
| 6,635,792 B2 | 10/2003 | Choi et al. ................... 585/489 |

FOREIGN PATENT DOCUMENTS

| | | | |
|---|---|---|---|
| DE | 19641149 | 4/1997 | |
| EP | 0390058 | 1/1990 | |
| EP | 0816311 | 1/1998 | |
| FR | 2761905 | 10/1998 | ............ B01J/29/20 |
| JP | 9-271640 | 10/1997 | ........... B01D/53/94 |

Primary Examiner—Christina Ildebrando
(74) Attorney, Agent, or Firm—Drinker Biddle & Reath LLP

(57) ABSTRACT

A catalyst for the disproportionation/transalkylation of various hydrocarbons consists of a carrier and a metal component supported on the carrier. The carrier comprises 10 to 80 wt % of mordenite and/or beta type zeolite with a mole ratio of silica/alumina ranging from 10 to 200; 0 to 70 wt % of ZSM-5 type zeolite with a mole ratio of silica/alumina ranging from 30 to 500; and 5 to 90 wt % of at least one inorganic binder selected from the group consisting of gamma-alumina, silica, silica alumina, bentonite, kaolin, clinoptilolite, and montmorillonite. The metal component comprises platinum and either tin or lead. The catalyst enables mixed xylenes to be produced at remarkably high yields from benzene, toluene and C9 or higher aromatic compounds through disproportionation/transalkylation with a great reduction in aromatic loss. In addition, the catalyst can maintain its catalytic activity for a long period of time without deactivation.

14 Claims, 1 Drawing Sheet

DISPROPORTIONATION/ TRANSALKYLATION OF AROMATIC HYDROCARBONS

This is a continuation of application Ser. No. 09/720,723, filed Dec. 26, 2000, now abandoned which is a 371 of PCT/KR99/00619, filed Oct. 14, 1999 and published in English.

BACKGROUND OF THE INVENTION

1. Field of the Invention

The present invention relates, in general, to a catalyst for the disproportionation/transalklylation of aromatic hydrocarbons and, more particularly, to a catalyst which is useful to prepare mixed xylenes from a mixture of benzene, toluene and C9 or higher aromatic compounds through disproportionation/transalklylation. Also, the present invention is concerned with a method for preparing such a catalyst.

2. Description of the Prior Art

Mixed xylenes, very important raw materials in the petrochemical industry, are composed of ethyl benzene and xylene isomers including meta-xylene, para-xylene and ortho-xylene. From mixed xylenes, thus, pure m-xylene, p-xylene and o-xylene, all important base fractions in the petrochemical industry, can be produced.

Owing to their similar boiling points, xylene isomers are very difficult to individually extract from the mixed xylenes by ordinary distillation processes. Usually, adsorptive separation, crystallization and/or isomerization are used to separate the individual isomers from the mixed xylenes.

To produce the mixed xylenes, the separation from the fractions fractions rich in the mixed xylenes and the synthesis by reaction are commercially utilized. The former includes the separation from the reformed oils produced during the reforming of naphtha and the separation from the thermally cracked oils which are produced as by-products during thermal cracking. As for the latter, it can be exemplified by the disproportionation of toluene, the transalkylation of toluene/C9 aromatic hydrocarbons, and the alkylation of toluene with methanol.

The disproportionation/transalkylation catalysts which are used for commercial purposes are usually based on zeolites, such as mordenite and ZSM-5. For use, these zeolites are either molded or impregnated with catalytic metal components.

In many prior patents are found zeolite-based disproportionation/transalkylation catalysts.

U.S. Pat. No. 4,083,886 discloses a catalyst for transalkylating alkyl aromatic compounds such as toluene, which is prepared by molding mordenite with an inorganic oxide binder after being treated with aqueous ammonia. In contrast with the present invention, this catalyst does not employ a metal capable of hydrogenation, but performs transalkylation by zeolite itself. Toluene alone can be smoothly transalkylated by this catalyst. From a reaction containing C9 or higher aromatic hydrocarbons, however, a high yield of the mixed xylenes cannot be expected because the reaction is hard to dealkylate with the catalyst. In addition, the catalyst is deactivated faster as the proportion of C9 or higher aromatic hydrocarbons becomes larger.

U.S. Pat. No. 5,030,787 discloses a transalkylating catalyst which is based on beta-zeolite whose acidity is weakened by a steam treatment. With the intent to reduce side products and to retard the deactivation of catalyst, the weakening of acidity is conducted. However, the weakening of the acidity without the introduction of a hydrogenating metal results in deteriorating the catalytic activity of the catalyst and thus, reducing the yield of the mixed xylenes.

U.S. Pat. No. 5,475,180 pertains to the disproportionation/transalkylation of toluene and high molecular weight aromatic hydrocarbons by use of a catalyst comprising nickel supported on mordenite. As in the present invention, the nickel functions to effectively dealkylate the aromatic hydrocarbons of large molecular weights and to suppress the deactivation of the catalyst. However, it is expected that this catalyst becomes deactivated faster during the catalytic reaction than does the catalyst employing activity-controlled platinum because the hydrogenation activity of nickel is far poorer than that of platinum. In addition, when sulfur compounds are introduced into the reaction, the hydrogenation activity of the nickel is greatly deteriorated owing to its strong association with the sulfur compounds. The feedstocks, which are fed into the commercial disproportionation/transalkylation process, usually undergo desulfurization in advance, but there is not completely excluded the possibility that sulfur compounds might flow into the disproportionation/transalkylation process owing to process accidents or operational errors. Upon the flowing in of sulfur compounds, the platinum catalyst has its platinum ingredient adsorbed with the sulfur compounds and thus, becomes deactivated temporarily. When the influx of sulfur compounds are stopped, however, the catalyst restores its catalytic activity because the sulfur compounds are desorbed from the platinum. In the case of nickel, the sulfur compounds, if adsorbed once, are very difficult to remove during reaction.

Another catalyst for the disproportionation/transalkylation of toluene and C9 aromatic hydrocarbons is found in U.S. Pat. No. 3,671,602 which discloses an alkali metal-deficient mordenite on which aluminum fluoride and a metal selected from the group consisting of Cu, Ag and Au or from the group consisting of W, Mo, Cr and As are supported, affirming that aluminum fluoride plays a role in restraining the production of coke so as to inhibit the deactivation of the catalyst. In this case the anti-deactivation effect cannot be efficiently conducted when the reaction contains C10 aromatic hydrocarbons or a high proportion of C9 aromatic hydrocarbons.

Also, the disproportionation/transalkylation of toluene and alkyl aromatic hydrocarbons is described in U.S. Pat. No. 4,723,048 which discloses a catalyst comprising mordenite on which a metal of Group VIII, such as nickel or palladium, a metal of Group IB, such as Ag, and a metal of Group IVA, such as Sn, Pb or Ge, are supported. In this patent, the metal of Group VIII, such as nickel or palladium, serves as a hydrogenating metal whose activity is controlled by the metal of Group IVA, thereby improving the performance of the catalyst. The metals such as nickel and palladium are significantly poor in hydrogenation activity as compared with platinum, used in the present invention. When the reaction gets a high content of C9 or higher aromatic hydrocarbons, the catalyst is difficult to protect from deactivation. In addition, the presence of sulfur compounds in the reaction may make the hydrogenating activity of the catalyst drop to an unrecoverable state.

U.S. Pat. No. 5,475,179 discloses a catalyst for the disproportionation of toluene, which is based on Si-treated ZSM-5 type zeolite. It is also described that the treatment of ZSM-5 type zeolite with silicon makes the shape selectivity of the ZSM-5 type zeolite increase, so that the selectivity for the p-xylene of the mixed xylenes produced upon the disproportionation of toluene comes to reach about 90 wt % which is far higher than the thermodynamic equilibrium, 24 wt %. The use of ZSM-5 type zeolite alone, however, can be applied for toluene only, but cannot be applied for the disproportionation or transalkylation of C9 or higher aromatic hydrocarbons because of its structural limit.

In addition, there are many examples of the disproportionation/transalkylation catalysts using mordenite, or beta type or ZSM-5 type zeolite as a base material, but nowhere is found a catalyst which uses platinum as a hydrogenating function and tin or lead as an activity controller so as to bring about a great improvement in the yield of mixed xylenes and in the deactivation of catalyst, as in the present invention.

SUMMARY OF THE INVENTION

The intensive and thorough research on the development of a catalyst for the disproportionation/transalkylation of aromatic hydrocarbons, repeated by the present inventors aiming to solve the problems, resulted in the finding that platinum, together with tin or lead which plays a role as a controller of the high hydrogenating activity of platinum, is capable of producing mixed xylenes at high yields and exceptionally preventing the catalyst deactivation when being supported on a carrier consisting of mordenite or beta type or ZSM-5 type zeolite and an inorganic binder.

Therefore, it is an object of the present invention, based on this finding, to overcome the problems encountered in prior arts and to provide a catalyst for the disproportionation/transalkylation of benzene, toluene and C9 aromatic hydrocarbons, which allows mixed xylenes to be produced at remarkably high yields from benzene, toluene and C9 or higher aromatic compounds through disproportionation/transalkylation with a great reduction in aromatic loss and can maintain its catalytic activity for a long period of time without deactivation.

It is another object of the present invention to provide a method for preparing such a catalyst.

In accordance with a first aspect of the present invention, there is provided a catalyst for the disproportionation/transalkylation of aromatic hydrocarbons, which comprises: a carrier comprising 10 to 80 wt % of mordenite and/or beta type zeolite with a mole ratio of silica/alumina ranging from 10 to 200; 0 to 70 wt % of ZSM-5 type zeolite with a mole ratio of silica/alumina ranging from 30 to 500; and 5 to 90 wt % of at least one inorganic binder selected from the group consisting of gamma-alumina, silica, silica alumina, bentonite, kaolin, clinoptilolite, and montmorillonite, and metal components, which are supported on the carrier, comprising platinum and either tin or lead, whereby mixed xylenes can be produced from benzene, toluene and C9 or higher aromatic hydrocarbons.

In accordance with a second aspect of the present invention, there is provided a method for preparing a catalyst for the disproportionation/transalkylation of various aromatic hydrocarbons, comprising the steps of a) forming a carrier which comprises 10 to 80 wt % of mordenite and/or beta type zeolite with a mole ratio of silica/alumina ranging from 10 to 200; 0 to 70 wt % of ZSM-5 type zeolite with a mole ratio of silica/alumina ranging from 30 to 500; and 5 to 90 wt % of at least one inorganic binder selected from the group consisting of gamma-alumina, silica, silica alumina, bentonite, kaolin, clinoptilolite, and montmorillonite; b) supporting 0.01 to 10.0 weight parts of tin or 0.01 to 7.0 weight parts of lead in 100 weight parts of the carrier on the carrier; and c) supporting 0.001 to 0.5 weight parts of platinum in 100 weight parts of the carrier on a tin or lead-supported carrier.

In accordance with a third aspect of the present invention, there is provided a method for preparing a catalyst for the disproportionation/transalkylation of various aromatic hydrocarbons, comprising the steps of: a) mixing 10 to 80 wt % of mordenite and/or beta type zeolite with a mole ratio of silica/alumina ranging from 10 to 200; 0 to 70 wt % of ZSM-5 type zeolite with a mole ratio of silica/alumina ranging from 30 to 500; 5 to 90 wt % of at least one inorganic binder selected from the group consisting of gamma-alumina, silica, silica alumina, bentonite, kaolin, clinoptilolite, and montmorillonite; 0.01 to 10.0 weight parts of tin or 0.01 to 7.0 weight parts of lead in 100 weight parts of the zeolite and the binder; and 0.001 to 0.5 weight parts of platinum in 100 weight parts of the zeolite and the binder; and b) molding the mixture.

In accordance with a fourth aspect of the present invention, there is provided a method for preparing a catalyst for the disproportionation/transalkylation of various aromatic hydrocarbons, comprising the steps of: a) supporting platinum on mordenite and/or beta type zeolite, ranging, in a mole ratio of silica/alumina, from 10 to 200, through impregnation or ion exchange; b) molding the platinum-supported mordenite and/or beta type zeolite with ZSM-5 type zeolite, ranging, in a mole ratio of silica/alumina, from 30 to 500 and at least one inorganic binder selected from the group consisting of gamma-alumina, silica, silica alumina, bentonite, kaolin, clinoptilolite, and montmorillonite, into a certain form in which the mordenite and/or beta type zeolite, the ZSM-5 type zeolite, and the inorganic binder are present at an amount of 10 to 80 wt %, 0 to 70 wt %, and 5 to 90 wt %, respectively, said platinum amounting to 0.001 to 0.5 weight parts based on 100 weight parts of a carrier consisting of the zeolites and the binder; and c) supporting tin or lead in the molded form at an amount of 0.01 to 10.0 weight parts or 0.01 to 7.0 weight parts, respectively, based on 100 weight parts of the carrier.

In accordance with a fifth aspect of the present invention, there is provided a method for preparing a catalyst for the disproportionation/transalkylation of various aromatic hydrocarbons, comprising the steps of: a) supporting platinum on a mixture of at least one of mordenite and beta type zeolite, and ZSM-5 zeolite which ranges, in a mole ratio of silica/alumina, from 10 to 200 and from 30 to 500, respectively, through impregnation or ion exchange; b) molding the platinum-supported zeolite, together with at least one inorganic binder selected from the group consisting of gamma-alumina, silica, silica alumina, bentonite, kaolin, clinoptilolite, and montmorillonite, into a certain form in which the mordenite and/or beta type zeolite, the ZSM-5 type zeolite, and the inorganic binder are present at an amount of 10 to 80 wt %, 0 to 70 wt %, and 5 to 90 wt %, respectively, said platinum amounting to 0.001 to 0.5 weight parts based on 100 weight parts of a carrier consisting of the zeolites and the binder; and c) supporting tin or lead in the molded form at an amount of 0.01 to 10.0 weight parts or 0.01 to 7.0 weight parts, respectively, based on 100 weight parts of the carrier.

In accordance with a sixth aspect of the present invention, there is provided a method for preparing a catalyst for the disproportionation/transalkylation of various aromatic hydrocarbons, comprising the steps of: a) supporting tin or lead on mordenite and/or beta type zeolite, ranging, in a mole ratio of silica/alumina, from 10 to 200, through impregnation or ion exchange; b) molding the tin or lead-supported mordenite and/or beta type zeolite with ZSM-5 type zeolite, ranging, in a mole ratio of silica/alumina, from 30 to 500 and at least one inorganic binder selected from the group consisting of gamma-alumina, silica, silica alumina, bentonite, kaolin, clinoptilolite, and montmorillonite, into a certain form in which the mordenite and/or beta type zeolite, the ZSM-5 type zeolite, and the inorganic binder are present at an amount of 10 to 80 wt %, 0 to 70 wt %, and 5 to 90 wt %, respectively, said tin amounting to 0.01 to 10.0 weight parts or said lead amounting to 0.01 to 7.0 weight parts based on 100 weight parts of a carrier consisting of the zeolites and the binder; and c) supporting platinum in the molded form at an amount of 0.001 to 0.5 weight parts based on 100 weight parts of the carrier.

In accordance with a seventh aspect of the present invention, there is provided a method for preparing a catalyst for the disproportionation/transalkylation of various aromatic hydrocarbons, comprising the steps of: a) supporting tin or lead on a mixture of at least one of mordenite and beta type zeolite, and ZSM-5 zeolite which ranges, in a mole ratio of silica/alumina, from 10 to 200 and from 30 to 500, respectively, through impregnation or ion exchange; b) molding the tin or lead-supported zeolite, together with at least one inorganic binder selected from the group consisting of gamma-alumina, silica, silica alumina, bentonite, kaolin, clinoptilolite, and montmorillonite, into a certain form in which the mordenite and/or beta type zeolite, the ZSM-5 type zeolite, and the inorganic binder are present at an amount of 10 to 80 wt %, 0 to 70 wt %, and 5 to 90 wt %, respectively, said tin amounting to 0.01 to 10.0 weight parts or said lead amounting to 0.01 to 7.0 weight parts based on 100 weight parts of a carrier consisting of the zeolites and the binder; and c) supporting platinum in the molded form at an amount of 0.001 to 0.5 weight parts based on 100 weight parts of the carrier.

DETAILED DESCRIPTION OF THE INVENTION

Figure 1:
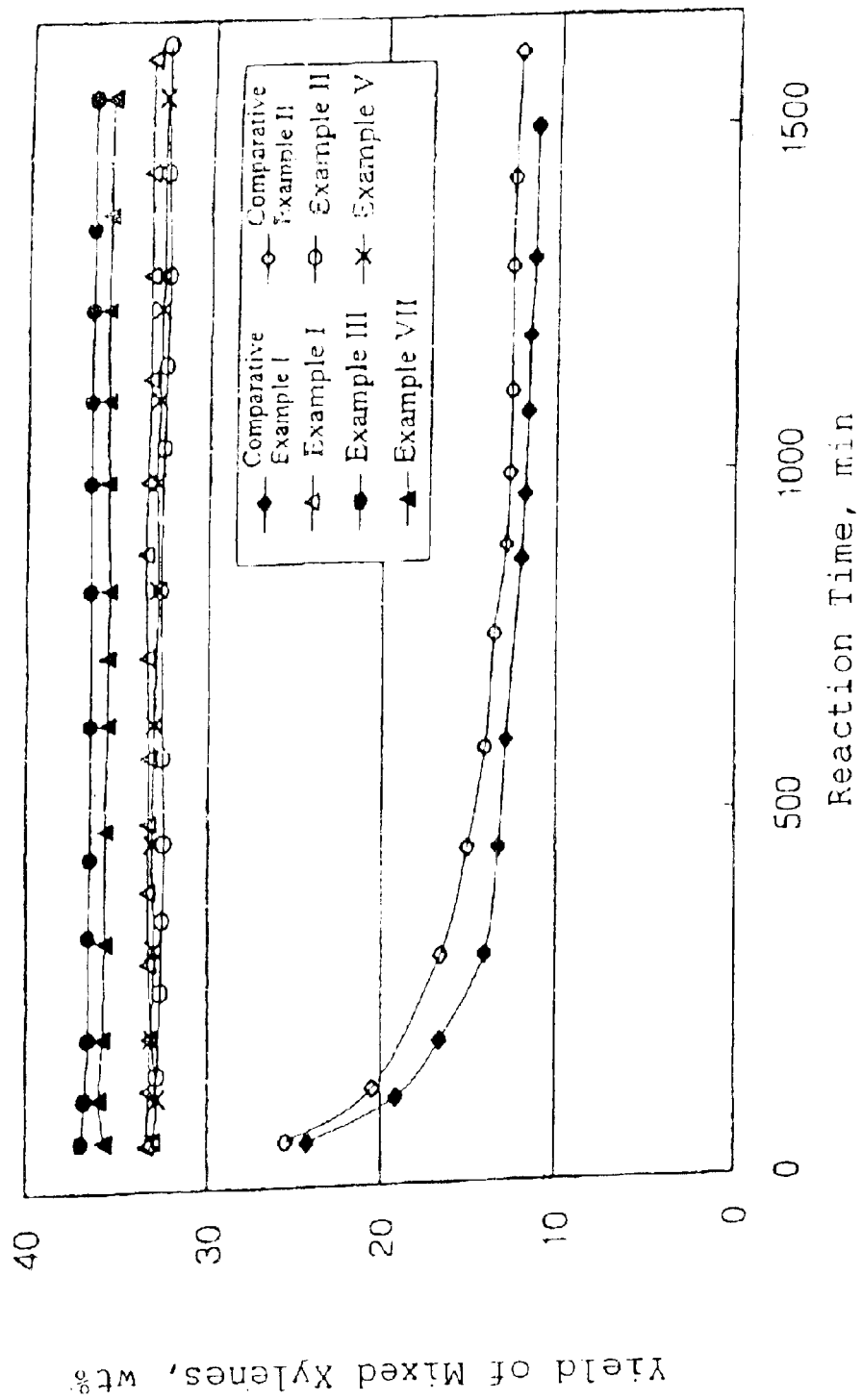
FIG. 1 is a graph in which the production yields of mixed xylenes are plotted with respect to reaction times for various catalysts.

The present invention pertains to a catalyst which is useful to mixed xylenes from benzene, toluene and C9 or higher aromatic hydrocarbons through disproportionation/transalkylation. On the catalyst, disproportionation between toluenes, transalkylation between toluene and C9 aromatic compounds, dealkylation of C9 or higher alkyl aromatic compounds, and transalkylation between benzene and C9 or higher aromatic hydrocarbons take place concurrently. This dealkylation is very important because toluene, needed for the disproportionation/transalkylation, is provided as a result of this reaction. Also, the transalkylation between benzene and C9 or higher aromatic hydrocarbons produces toluene and mixed xylenes.

In producing mixed xylenes from benzene, toluene and C9 or higher aromatic hydrocarbons, the olefins resulting from the dealkylation, such as ethylene and propylene, must be quickly hydrogenated; otherwise, the olefins are re-alkylated to the aromatic hydrocarbons, resulting in a decrease in the conversion rate of the C9 or higher aromatic hydrocarbons. Further, the olefins themselves are oligomerized to promote the production of cokes which give rise to deactivation in the catalyst. Herein, it should be noted that a metal capable of hydrogenation is contained, along with a zeolite base, such as mordenite, beta or ZSM-5, in the catalyst.

As a hydrogenating function, platinum is used in accordance with the present invention. To appropriately control the hydrogenating activity of platinum, tin or lead is employed. For better catalytic performance, this controlling metal is preferably used at an amount at least three times more than that of platinum.

Mordenite, beta and ZSM-5, which are useful zeolites in the present invention, are synthesized in sodium forms at first. The sodium forms are subjected to ion exchange with ammonium chloride or ammonium nitrate and these ammonium forms can be readily converted into hydrogen forms by calcination. In the present invention, an ammonium or hydrogen form of mordenite, beta or ZSM-5 is taken.

In accordance with the present invention, the mordenite or beta preferably ranges, in the mole ratio of silica/alumina, from 10 to 200. For instance, if the mole ratio of silica/alumina is below 10, the catalyst has too potent catalytic activity with an increasing of by-products and is deactivated too fast. On the other hand, if the zeolite has too high a mole ratio of silica/alumina, the resulting catalyst is so weak in catalytic activity that the production yield of mixed xylenes is poor.

As for ZSM-5, it preferably has a mole ratio of silica/alumina from 30 to 500. As in the mordenite or beta, the mole ratio less than 30 provides the catalyst with too potent catalytic activity which causes an increase in by-products, forcing the catalyst to be deactivated too fast. On the other hand, if the mole ratio exceeds 500, the catalyst exerts a weak catalytic action on the aromatic hydrocarbons with a reduction in the production yield of mixed xylenes.

According to the present invention, the zeolites are combined with at least one inorganic binder. Examples of the inorganic binder usable in the present invention include gamma alumina, silica, silica alumina, bentonite, kaolin, clinoptilolite, and montmorillonite with preference to amorphous inorganic oxides of gamma alumina, silica and silica alumina and most preference to gamma alumina and silica.

When combining the inorganic binder with mordenite or beta, and ZSM-5 to give a carrier, the mordenite or beta is preferably used at an amount of 10 to 80 wt %, ZSM-5 at an amount of 0 to 70 wt % and the inorganic binder at an amount of 5 to 90 wt %. For example, if the content of mordenite or beta is below 10 wt %, there is a deterioration in the production yield of mixed xylenes. On the other hand, a content greater than 80 wt % causes a problem of weakening the mechanical strength of the catalyst. ZSM-5, if used at an amount exceeding 70 wt %, has a bad effect on the production yield of mixed xylenes. As for the amount of the inorganic binder, less than 5 wt % causes a weakening in the mechanical strength of the catalyst while more than 90 wt % has a problem of lowering the production yield of mixed xylenes.

The mixture of mordenite or beta, ZSM-5 and the inorganic binder is extruded into a cylindrical shape in catalyst grains are 2 mm in diameter and 5 to 15 mm in length. Alternatively, the catalyst may be molded into a spherical shape. It should be noted that the catalyst may have any form. The molded carrier made of mordenite or beta, ZSM-5 and the inorganic binder preferably has the following physical properties: an apparent bulk density of 0.4 to 0.8 cc/g, an average pore diameter of 50 to 200 Å, a pore volume of 0.1 to 1 cc/g, and a specific surface area of 200 to 400 m²/g.

After the molding of mordenite or beta, ZSM-5 and the inorganic binder, the carrier is provided to make platinum/tin or platinum/lead supported thereon. Alternatively, the metal components may be supported on a mixture of mordenite or beta, and ZSM-5 before being molded along with the inorganic binder. The metal components may be introduced regardless of the time when the molding is conducted. Also, whether supporting the metal components before or after the molding, either of the two metals may be introduced first. Regardless of which of them is first introduced, there is a little difference in catalytic activity. Alternatively, the two metal components may be introduced concurrently. For example, the two metals are combined with the carrier mixture and then, molded together. Alternatively, either of them is combined with the carrier mixture before molding and then, the rest is supported on the resulting carrier to give a catalyst.

Platinum is preferably used at an amount of approximately 0.001 to 0.5 weight parts based on 100 weight parts of the carrier consisting of mordenite or beta, ZSM-5 and the inorganic binder. For example, if too little platinum is used, the resulting catalyst becomes of poor activity in terms of the dealkylation of alkyl aromatic compounds with reduction in the production yield of mixed xylenes while the catalyst is deactivated too fast. On the other hand, if platinum is used at an amount more than 0.5 weight parts based on 100 weight parts of the carrier, the resulting catalyst has too potent platinum activity, performing an active hydrocracking function to produce a significant amount of low molecular weight hydrocarbons (C1~C5).

The introduction of platinum to the catalyst structure may be achieved by ion exchange, impregnation or a physical mixing process. Upon the introduction by ion exchange, a solution of tetraamineplatinum chloride or tetraamine platinum nitrate in water may be used as a precursor for the platinum component. For the impregnation, a solution of hydrogen hexachloroplatinate or tetraamineplatinum chloride in water is used as a precursor for the platinum component. When a physical mixing process is taken to introduce platinum, any of the aqueous platinum solutions may be used.

In accordance with the present invention, tin, playing an important role in controlling the activity of the platinum, is preferably used at an amount of approximately 0.01 to 10.0 weight parts based on 100 weight parts of the carrier comprising mordenite or beta, ZSM-5 and the inorganic binder. For example, if the amount of tin exceeds 10.0 weight parts based on 100 weight parts of the carrier, the performance of platinum becomes so weak that there are caused problems of decreasing the production yield of mixed xylenes and promoting the deactivation of the catalyst. Lower than 0.01 weight parts of tin is insufficient to control the performance of platinum, resulting in high contents of low molecular weight hydrocarbons in the products. Tin is preferably introduced into the catalyst through impregnation or mixing. As a precursor for the tin component, stannous chloride, stannic chloride, tin acetate, or tin sulfate may be used.

In accordance with the present invention, lead may be used instead of tin. In the case of employing lead, the introduction of lead may be conducted in the same manner as in tin, with respect to amount, introduction route and precursor. It is preferred that the amount of lead is on the order of approximately 0.01 to 7.0 weight parts based on 100 weight parts of the carrier comprising mordenite or beta, ZSM-5 and the inorganic binder. In the catalyst, lead performs the same functions as tin and shows the same effects as those that tin does in dependence on its amount. Preferably, lead is introduced through impregnation or mixing. A precursor for the lead component may be selected from lead acetate, lead nitrate and lead sulfate.

After the introduction of the metal components related to hydrogenating functions is completed, the catalyst undergoes a drying process in air. It is preferable that the drying is conducted at a temperature of 60 to 200° C. for a period of 0.5 to 12 hours. Following the drying, a calcination process is applied for the catalyst. Preferably, the calcination process is carried out at a temperature of 300 to 650° C. for a period of 1 to 12 hours.

As previously mentioned, a pair of Pt/Sn or Pt/Pb, when being introduced onto the carrier comprising mordenite or beta, ZSM-5 and the inorganic binder, are indifferent to their introduction order. Instead, it is very important to make the metals associated suitably with each other. In order to provide better catalytic activity, particularly, platinum is in association with tin or lead or in the proximity of tin or lead sufficiently to have electrical and chemical influence on each other greater than does exist independently in the catalyst.

Platinum, if being in an independent state in the catalyst, exerts its high hydrogenation activity without control, effecting side reactions as above mentioned. However, when in association with or sufficiently near tin or lead, platinum is subject to tin or lead in its hydrogenation activity, so an optimal production yield of mixed xylenes can be obtained with sufficient retardation of the deactivation of the catalyst.

Being useful for the disproportionation of toluene and the transalkylation of toluene/C9 aromatic hydrocarbons, the catalyst according to the present invention is able to exert its effective performance when toluene or C9 or higher aromatic hydrocarbons (C9~C11 aromatic hydrocarbons) are fed, alone or in combination irrespective of their mole ratio of toluene/C9 or higher aromatic hydrocarbons and even when benzene is further fed.

As a result of subjecting benzene, toluene and C9 or higher aromatic hydrocarbons to disproportionation/transalkylation on the catalyst of the present invention, mixed xylenes were obtained at a yield of about 32 to 37 wt % with an aromatic loss amounting to as low as 2 wt %.

A better understanding of the present invention may be obtained in light of the following examples which are set forth to illustrate, but are not to be construed to limit the present invention.

COMPARATIVE EXAMPLE I

A hydrogen form of mordenite with a mole ratio of silica/alumina of 90 was molded, together with gamma alumina as a binder, into a cylindrical shape 2 mm in diameter and 10 mm in length, so as to give a carrier in which the mordenite amounted to 50 wt %. After being dried at 150° C. for 10 hours, the carrier was calcined at 500° C. for 3 hours.

Without being further introduced with any metal, the carrier was tested for disproportionation/transalkylation. To this end, 2 g of the carrier were charged in a fixed-bed reactor and subjected to reduction at 400° C. for 2 hours in a hydrogen atmosphere. In the presence of the catalyst thus obtained, benzene, toluene and C9 or higher aromatic hydrocarbons were allowed to be subjected to disproportionation/transalkylation. The reaction results are given, along with reaction conditions, in Table 1 and FIG. 1.

COMPARATIVE EXAMPLE II

A catalyst was prepared in the same manner as that of Comparative Example I, except for using a hydrogen form of beta zeolite with a mole ratio of silica/alumina of 25. The catalyst was tested for disproportionation/transalkylation as in Comparative Example I. The results are given as shown in Table 1.

COMPARATIVE EXAMPLE III

A hydrogen form of mordenite with a mole ratio of silica/alumina of 90 and a hydrogen form of ZSM-5 with a mole ratio of silica/alumina of 80 were molded, together with gamma alumina as a binder, into a cylindrical shape 2 mm in diameter and 10 mm in length, so as to give a carrier in which the mordenite amounted to 50 wt %. After being dried at 150° C. for 10 hours, the carrier was calcined at 500° C. for 3 hours.

Without being further introduced with any metal, the carrier was tested for disproportionation/transalkylation under the same conditions as in Comparative Example I, but using a reactant mixture indicated in Table 1. The reaction results are given, along with reaction conditions, in Table 1 and FIG. 1.

COMPARATIVE EXAMPLE IV

A catalyst was prepared in the same manner as that of Comparative Example I, except for using a hydrogen form of beta zeolite with a mole ratio of silica/alumina of 25, instead of mordenite. The catalyst was tested for disproportionation/transalkylation as in Comparative Example III. The reaction results are given as shown in Table 1.

COMPARATIVE EXAMPLE V

After being prepared in the same manner as that of Comparative Example I, a carrier was treated with an aqueous $H_2PtCl_6$ solution such that 0.02 weight parts of platinum were impregnated in 100 weight parts of the carrier which was, then, dried at 150° C. for 10 hours, followed by calcination at 500° C. for 3 hours to give a catalyst. This was tested for the same disproportionation/transalkylation as in Comparative Example I, but using the reactant mixture indicated in Table 1. The reaction results are given in Table 1.

COMPARATIVE EXAMPLE VI

A carrier was prepared in the same manner as in Comparative Example II and introduced with platinum under the same condition as in Comparative Example II to give a catalyst in the presence of which disproportionation/transalkylation was conducted as in Comparative Example V. The reaction results are given in Table 1.

COMPARATIVE EXAMPLE VII

After being prepared in the same manner as that of Comparative Example III, a carrier was treated with an aqueous $H_2PtCl_6$ solution such that 0.02 weight parts of platinum were impregnated in 100 weight parts of the carrier which was, then, dried at 150° C. for 10 hours, followed by calcination at 500° C. for 3 hours to give a catalyst. This was tested for the same disproportionation/transalkylation as in Comparative Example I, but using the reactant mixture indicated in Table 1. The reaction condition and results are given in Table 1.

COMPARATIVE EXAMPLE VIII

A carrier was prepared in the same manner as in Comparative Example IV and introduced with platinum under the same condition as in Comparative Example VII to give a catalyst in the presence of which disproportionation/transalkylation was conducted as in Comparative Example VII. The reaction results are given in Table 1.

TABLE 1

Assay for Disproportionation/Transalkylation Performance

| Nos. of C. Exmpl. | Aromatic Reactants (wt %) | | | Aromatic Products (wt %) | | | Yield of mixed xylenes (wt %) | Aromatic Loss (wt %) |
|---|---|---|---|---|---|---|---|---|
| | C6–C8 | C9 | C10 | C6–C8 | C9 | C10 | | |
| I | 51.2 | 45.1 | 3.5 | 58.4 | 36.8 | 4.5 | 11.8 | 0.3 |
| II | 51.2 | 45.1 | 3.5 | 58.8 | 36.6 | 4.5 | 12.1 | 0.2 |
| III | 22.1 | 74.1 | 2.6 | 59.6 | 30.8 | 7.1 | 22.8 | 0.2 |
| IV | 22.1 | 74.1 | 2.6 | 58.4 | 31.0 | 7.5 | 22.5 | 0.2 |
| V | 22.1 | 74.1 | 2.6 | 64.1 | 9.6 | 1.4 | 26.4 | 22.8 |
| VI | 22.1 | 74.1 | 2.6 | 63.5 | 10.0 | 1.5 | 25.5 | 21.0 |
| VII | 22.1 | 74.1 | 2.6 | 63.0 | 23.6 | 1.0 | 23.1 | 10.2 |
| VIII | 22.1 | 74.1 | 2.6 | 62.5 | 24.0 | 1.2 | 22.5 | 11.0 |

Reaction condition:
Temp. 400° C.; Press. 27.9 kg/cm$^2$, WHSV = 3 hr$^{-1}$; H2/HC molar ratio = 3

EXAMPLE I

A hydrogen form of mordenite with a mole ratio of silica/alumina of 90 was molded, together with gamma alumina as a binder, into a cylindrical shape 2 mm in diameter and 10 mm in length, so as to give a carrier in which the mordenite amounted to 50 wt %. After being dried at 150° C. for 10 hours, the carrier was calcined at 500° C. for 3 hours. Using an aqueous $SnCl_2$ solution, 0.5 weight parts of tin were impregnated in 100 weight parts of the carrier, which was then dried at 150° C. for 10 hours and calcined at 500° C. for 3 hours. This tin-impregnated carrier was treated with an aqueous $H_2PtCl_6$ solution such that 0.05 weight parts of platinum were impregnated in 100 weight parts of the mordenite and binder. The resulting carrier was subjected to drying at 150° C. for 10 hours and then to calcination at 500° C. for 3 hours to allow a catalyst.

For disproportionation/transalkylation testing, 2.0 g of the catalyst were charged in a fixed-bed reactor and subjected to reduction at 400° C. for 2 hours in a hydrogen atmosphere. In the presence of the catalyst thus activated, benzene, toluene and C9 or higher aromatic hydrocarbons were allowed to be subjected to disproportionation/transalkylation. The reaction results are given, along with reaction conditions, in Table 2 and FIG. 1.

EXAMPLE II

A catalyst was prepared in the same manner as that of Example I, except for using a hydrogen form of beta zeolite with a mole ratio of silica/alumina of 25. The catalyst was tested for disproportionation/transalkylation as in Example I, but using the reactant mixture indicated in Table 2. The results are given as shown in Table 2 and FIG. 1. As apparent from the data, this catalyst showed similar catalytic performance to that of the catalyst of Example I.

EXAMPLE III

A hydrogen form of mordenite and a hydrogen form of ZSM-5 which had mole ratios of silica/alumina of 90 and 80, respectively, were molded, together with gamma alumina as a binder, into a cylindrical shape 2 mm in diameter and 10 mm in length, so as to give a carrier in which the mordenite and the ZSM-5 amounted to 40 wt % and 15 wt %, respectively. After being dried at 150° C. for 10 hours, the carrier was calcined at 500° C. for 3 hours. Using an aqueous $SnCl_2$ solution, 0.5 weight parts of tin were impregnated in 100 weight parts of the carrier, which was then dried at 150° C. for 10 hours and calcined at 500° C. for 3 hours. This tin-impregnated carrier was treated with an aqueous $H_2PtCl$ solution such that 0.05 weight parts of platinum were impregnated in 100 weight parts of the mordenite, ZSM-5 and binder. The resulting carrier was subjected to drying at 150° C. for 10 hours and then to calcination at 500° C. for 3 hours to allow a catalyst.

The catalyst was tested for disproportionation/transalkylation under the same conditions as in Example I, but using a reactant mixture indicated in Table 2. The reaction results are given in Table 2 and FIG. 1. The catalyst showed a similar reaction performance to and a little bit more improved production yield of mixed xylenes than the catalyst of Example I.

EXAMPLE IV

A catalyst was prepared in the same manner as that of Example III, except for using a hydrogen form of beta zeolite with a mole ratio of silica/alumina of 25, instead of mordenite, and tested for disproportionation/transalkylation as in Example III. The reaction results are given as shown in Table 2. There was obtained a similar performance to that of Example III.

EXAMPLE V

While a hydrogen form of mordenite with a mole ratio of silica/alumina of 90 was molded, together with gamma-alumina as a binder, into a cylindrical shape 2 mm in diameter and 10 mm in length, an aqueous $H_2PtCl_6$ solution and an aqueous $SnCl_2$ solution were added so as to make platinum and tin be present at amounts of 0.04 and 0.4 weight parts, respectively, in 100 weight parts of the carrier consisting of the mordenite and the binder with the mordenite amounting to 50 wt %. Thereafter, the carrier was dried at 150° C. for 10 hours, followed by calcination at 500° C. for 3 hours to give a catalyst. This was tested for the same disproportionation/transalkylation as in Example I. The reaction conditions and results are given in Table 2 and FIG. 1.

EXAMPLE VI

A catalyst was prepared in the same manner as that of Example V, except for using a hydrogen form of beta zeolite with a mole ratio of silica/alumina of 25, instead of mordenite, and tested for disproportionation/transalkylation as in Example V. The reaction results are given as shown in Table 2.

EXAMPLE VII

While hydrogen forms of mordenite and ZSM-5 which had mole ratios of silica/alumina of 90 and 80, respectively, were molded, together with gamma-alumina as a binder, into a cylindrical shape 2 mm in diameter and 10 mm in length, an aqueous $H_2PtCl_6$ solution and an aqueous $SnCl_2$ solution were added so as to make platinum and tin be present at amounts of 0.04 and 0.4 weight parts, respectively, in 100 weight parts of the carrier consisting of the mordenite, ZSM-5 and the binder with the mordenite and the ZSM-5 amounting to 40 wt % and 15 wt %, respectively. Thereafter, the carrier was dried at 150° C. for 10 hours, followed by calcination at 500 ° C. for 3 hours to allow a catalyst. This was tested for the same disproportionation/transalkylation as in Example I, but using the reactant mixture indicated in Table 2. The reaction conditions and results are given in Table 2 and FIG. 1.

EXAMPLE VIII

A catalyst was prepared in the same manner as that of Example VII, except for using a hydrogen form of beta zeolite with a mole ratio of silica/alumina of 25, instead of mordenite and ZSM-5, and tested for disproportionation/transalkylation as in Example VII. The reaction results are given as shown in Table 2.

TABLE 2

| | Assay for Disproportionation/Transalkylation Performance | | | | | | | |
|---|---|---|---|---|---|---|---|---|
| Nos. of Exmpl. | Aromatic Reactants (wt %) | | | Aromatic Products (wt %) | | | Yield of mixed xylenes (wt %) | Aromatic Loss (wt %) |
| | C6–C8 | C9 | C10 | C6–C8 | C9 | C10 | | |
| I | 65.5 | 31.0 | 2.9 | 80.3 | 12.8 | 3.2 | 33.3 | 1.3 |
| II | 65.5 | 31.0 | 2.9 | 79.8 | 12.6 | 3.0 | 32.5 | 1.4 |
| III | 22.1 | 74.1 | 2.6 | 63.6 | 21.5 | 4.2 | 36.4 | 1.9 |
| IV | 22.1 | 74.1 | 2.6 | 62.6 | 22.5 | 4.9 | 35.3 | 1.7 |
| V | 65.5 | 31.0 | 2.9 | 81.8 | 11.3 | 1.7 | 33.0 | 1.8 |
| VI | 65.5 | 31.0 | 2.9 | 79.5 | 12.6 | 2.9 | 32.1 | 2.3 |

TABLE 2-continued

Assay for Disproportionation/Transalkylation Performance

| Nos. of Exmpl. | Aromatic Reactants (wt %) | | | Aromatic Products (wt %) | | | Yield of mixed xylenes (wt %) | Aromatic Loss (wt %) |
|---|---|---|---|---|---|---|---|---|
| | C6–C8 | C9 | C10 | C6–C8 | C9 | C10 | | |
| VII | 22.1 | 74.1 | 2.6 | 63.1 | 21.6 | 4.5 | 35.7 | 1.8 |
| VIII | 22.1 | 74.1 | 2.6 | 62.7 | 22.0 | 5.0 | 35.0 | 1.6 |

Reaction condition:
Temp. 400° C.; Press. 27.9 kg/cm$^2$, WHSV = 3 hr$^{-1}$; H2/HC molar ratio = 3

From the data of Table 2, it is recognized that mixed xylenes can be produced at even much higher yields using the catalysts according to the present invention than using the conventional catalysts. In addition, the catalyst of Examples I to VIII show significantly lowered aromatic loss as compared with the catalysts of Comparative Examples V to VIII.

With reference to FIG. 1, the production yields of mixed xylenes are traced with respect to reaction times for various catalysts. As shown in this graph, the catalysts according to the present invention maintain their activity constant through the reaction periods of time and thus, greatly improved in the catalyst deactivation compared with the conventional catalysts which are greatly deactivated within 500 min after the reaction.

EXAMPLE IX

The same procedure as that of Example I was repeated, except for using an aqueous Pb(NO$_3$)$_2$ solution instead of an aqueous SnCl$_2$ solution, to give a catalyst which contained lead at an amount of 0.6 weight parts based on 100 weight parts of the carrier. The catalyst was tested for disproportionation/transalkylation as in Example I, but using the reactant mixture indicated in Table 3. The reaction results are given in Table 3.

EXAMPLE X

The same procedure as that of Example II was repeated, except for using an aqueous Pb(NO$_3$)$_2$ solution instead of an aqueous SnCl$_2$ solution, to give a catalyst which contained lead at an amount of 0.6 weight parts based on 100 weight parts of the carrier. The catalyst was tested for disproportionation/transalkylation as in Example II, but using the reactant mixture indicated in Table 3. The reaction results are given in Table 3.

EXAMPLE XI

The same procedure as that of Example III was repeated, except for using an aqueous Pb(NO$_3$)$_2$ solution instead of an aqueous SnCl$_2$ solution, to give a catalyst which contained lead at an amount of 0.6 weight parts based on 100 weight parts of the carrier. The catalyst was tested for disproportionation/transalkylation as in Example III, but using the reactant mixture indicated in Table 3. The reaction results are given in Table 3.

EXAMPLE XII

The same procedure as that of Example IV was repeated, except for using an aqueous Pb(NO$_3$)$_2$ solution instead of an aqueous SnCl$_2$ solution, to give a catalyst which contained lead at an amount of 0.6 weight parts based on 100 weight parts of the carrier. The catalyst was tested for disproportionation/transalkylation as in Example IV, but using the reactant mixture indicated in Table 3. The reaction results are given in Table 3.

EXAMPLE XIII

The same procedure as that of Example V was repeated, except for using an aqueous Pb(NO$_3$)$_2$ solution, instead of an aqueous SnCl$_2$ solution, to give a catalyst which contained lead at an amount of 0.5 weight parts based on 100 weight parts of the carrier. The catalyst was tested for disproportionation/transalkylation as in Example V, but using the reactant mixture indicated in Table 3. The reaction results are given in Table 3.

EXAMPLE XIV

The same procedure as that of Example VI was repeated, except for using an aqueous Pb(NO$_3$)$_2$ solution instead of an aqueous SnCl$_2$ solution, to give a catalyst which contained lead at an amount of 0.5 weight parts based on 100 weight parts of the carrier. The catalyst was tested for disproportionation/transalkylation as in Example VI, but using the reactant mixture indicated in Table 3. The reaction results are given in Table 3.

EXAMPLE XV

The same procedure as that of Example VII was repeated, except for using an aqueous Pb(NO$_3$)$_2$ solution instead of an aqueous SnCl$_2$ solution, to give a catalyst which contained lead at an amount of 0.5 weight parts based on 100 weight parts of the carrier. The catalyst was tested for disproportionation/transalkylation as in Example VII, but using the reactant mixture indicated in Table 3. The reaction results are given in Table 3.

EXAMPLE XVI

The same procedure as that of Example VIII was repeated, except for using an aqueous Pb(NO$_3$)$_2$ solution instead of an aqueous SnCl$_2$ solution, to give a catalyst which contained lead at an amount of 0.5 weight parts based on 100 weight parts of the carrier. The catalyst was tested for disproportionation/transalkylation as in Example VIII, but using the reactant mixture indicated in Table 3. The reaction results are given in Table 3.

TABLE 3

Assay for Disproportionation/Transalkylation Performance

| Nos. of Exmpl. | Aromatic Reactants (wt %) | | | Aromatic Products (wt %) | | | Yield of mixed xylenes (wt %) | Aromatic Loss (wt %) |
|---|---|---|---|---|---|---|---|---|
| | C6–C8 | C9 | C10 | C6–C8 | C9 | C10 | | |
| IX | 21.1 | 63.9 | 13.3 | 61.3 | 18.7 | 8.2 | 33.5 | 1.8 |
| X | 21.1 | 63.9 | 13.3 | 60.1 | 19.3 | 8.9 | 33.0 | 1.5 |
| XI | 22.1 | 74.1 | 2.6 | 64.0 | 21.1 | 4.3 | 36.6 | 2.0 |
| XII | 22.1 | 74.1 | 2.6 | 64.3 | 20.9 | 4.1 | 36.8 | 2.2 |
| XIII | 22.1 | 74.1 | 2.6 | 61.7 | 18.5 | 7.9 | 33.7 | 1.9 |
| XIV | 22.1 | 74.1 | 2.6 | 61.3 | 18.8 | 8.1 | 33.0 | 1.9 |
| XV | 22.1 | 74.1 | 2.6 | 62.0 | 22.3 | 5.0 | 35.3 | 1.4 |
| XVI | 22.1 | 74.1 | 2.6 | 61.5 | 22.8 | 5.3 | 36.7 | 1.2 |

Reaction condition:
Temp. 400° C.; Press. 27.9 kg/cm$^2$, WHSV = 3 hr$^{-1}$; H2/HC molar ratio = 3

EXAMPLE XVII

After being impregnated with platinum by use of an aqueous H$_2$PtCl$_6$ solution, a hydrogen form of mordenite with a mole ratio of silica/alumina of 90 was molded, together with gamma alumina as a binder, into a cylindrical shape 2 mm in diameter and 10 mm in length, so as to give a platinum-impregnated carrier in which the mordenite amounted to 50 wt % based on the total weight of the carrier consisting of the mordenite and the gamma alumina binder and the platinum amounted to 0.04 weight parts based on 100 weight parts of the carrier. The platinum-impregnated carrier was dried at 150° C. for 10 hours and then, calcined at 500° C. for 3 hours. Using an aqueous SnCl$_2$ solution, 0.4 weight parts of tin were impregnated in 100 weight parts of the carrier, which was then dried at 150° C. for 10 hours and calcined at 500° C. for 3 hours to allow a catalyst.

The catalyst was tested for disproportionation/transalkylation under the same conditions as in Example I, but using a reactant mixture indicated in Table 4. The reaction results are given in Table 4.

EXAMPLE XVIII

A catalyst was prepared in the same manner as that of Example XVII, except for using a hydrogen form of beta zeolite with a mole ratio of silica/alumina of 25. The catalyst was tested for disproportionation/transalkylation as in Example XVII. The results are given as shown in Table 4.

EXAMPLE XIX

After being impregnated with platinum by use of an aqueous H$_2$PtCl$_6$ solution, a hydrogen form of mordenite with a mole ratio of silica/alumina of 90 was mixed with ZSM-5 with a mole ratio of silica/alumina of 80, after which this mixture was molded, together with gamma alumina as a binder, into a cylindrical shape 2 mm in diameter and 10 mm in length, so as to give a platinum-impregnated carrier in which the mordenite and the ZSM-5 amounted to 40 wt % and 15 wt %, respectively, based on the total weight of the carrier consisting of the mordenite, the ZSM-5 and the gamma alumina and the platinum amounted to 0.04 weight parts based on 100 weight parts of the carrier. The platinum-impregnated carrier was dried at 150° C. for 10 hours and then, calcined at 500° C. for 3 hours. Using an aqueous SnCl$_2$ solution, 0.4 weight parts of tin were impregnated in 100 weight parts of the carrier, which was then dried at 150° C. for 10 hours and calcined at 500° C. for 3 hours to allow a catalyst.

The catalyst was tested for disproportionation/transalkylation under the same conditions as in Example I, but using a reactant mixture indicated in Table 4. The reaction results are given in Table 4.

EXAMPLE XX

A catalyst was prepared in the same manner as that of Example XIX, except for using a hydrogen form of beta zeolite with a mole ratio of silica/alumina of 25. The catalyst was tested for disproportionation/transalkylation as in Example XIX, but using the reactant mixture indicated in Table 4. The results are given as shown in Table 4.

EXAMPLE XXI

A mixture of a hydrogen form of mordenite and a hydrogen form of ZSM-5 which had mole ratios of silica/alumina of 90 and 80, respectively, was treated with an aqueous H$_2$PtCl$_6$ solution such that platinum was impregnated at an amount of 0.075 wt % in the mordenite and at an amount of 0.067 wt % in the ZSM-5. Thereafter, the resulting mixture was molded, together with gamma alumina as a binder, into a cylindrical 2 mm in diameter and 10 mm in length, so as to give a platinum-impregnated carrier in which the mordenite and the ZSM-5 amounted to 40 wt % and 15 wt %, respectively, based on the total weight of the carrier consisting of the mordenite, the ZSM-5 and the gamma alumina. The platinum-impregnated carrier was dried at 150° C. for 10 hours and then, calcined at 500° C. for 3 hours. Using an aqueous SnCl$_2$ solution, 0.4 weight parts of tin were impregnated in 100 weight parts of the carrier, which was then dried at 150° C. for 10 hours and calcined at 500° C. for 3 hours to allow a catalyst.

The catalyst was tested for disproportionation/transalkylation under the same conditions as in Example I, but using a reactant mixture indicated in Table 4. The reaction results are given in Table 4.

EXAMPLE XXII

A catalyst was prepared in the same manner as that of Example XXI, except for using a hydrogen form of beta zeolite with a mole ratio of silica/alumina of 25. The catalyst was tested for disproportionation/transalkylation as in Example XXI. The results are given as shown in Table 4.

EXAMPLE XXIII

A catalyst was prepared in the same manner as that of Example XVII, except that an aqueous Pb(NO$_3$)$_2$ solution, instead of an aqueous SnCl$_2$ solution, was used to impregnate of 0.5 weight parts of lead in 100 weight parts of the carrier. The catalyst was tested for disproportionation/transalkylation as in Example XVII. The results are given as shown in Table 4.

EXAMPLE XXIV

A catalyst was prepared in the same manner as that of Example XXI, except that an aqueous Pb(NO$_3$)$_2$ solution, instead of an aqueous SnCl$_2$ solution, was used to impregnate 0.5 weight parts of lead in 100 weight parts of the carrier. The catalyst was tested for disproportionation/transalkylation as in Example XXI. The results are given as shown in Table 4.

ratio of silica/alumina of 90 was mixed with ZSM-5 with a mole ratio of silica/alumina of 80, after which this mixture was molded, together with gamma alumina as a binder, into a cylindrical shape 2 mm in diameter and 10 mm in length, so as to give a tin-impregnated carrier in which the mordenite and the ZSM-5 amounted to 40 wt % and 15 wt %, respectively, based on the total weight of the carrier consisting of the mordenite, the ZSM-5 and the gamma alumina and the tin amounted to 0.4 weight parts based on 100 weight parts of the carrier. The tin-impregnated carrier was dried at 150° C. for 10 hours and then, calcined at 500° C. for 3 hours. The resulting tin-contained carrier was treated with an aqueous H$_2$PtCl$_6$ solution such that 0.04 weight parts of platinum were impregnated in 100 weight parts of the carrier consisting of the mordenite, the ZSM-5 and the

TABLE 4

Assay for Disproportionation/Transalkylation Performance

| Nos. of Exmpl. | Aromatic Reactants (wt %) | | | Aromatic Products (wt %) | | | Yield of mixed xylenes (wt %) | Aromatic Loss (wt %) |
|---|---|---|---|---|---|---|---|---|
| | C6–C8 | C9 | C10 | C6–C8 | C9 | C10 | | |
| XVII | 21.1 | 63.9 | 13.3 | 61.0 | 18.1 | 7.8 | 33.1 | 1.6 |
| XVIII | 21.1 | 63.9 | 13.3 | 60.2 | 18.0 | 7.6 | 32.3 | 1.7 |
| XIX | 22.1 | 74.1 | 2.6 | 63.0 | 20.5 | 4.6 | 35.5 | 1.7 |
| XX | 22.1 | 74.1 | 2.6 | 62.5 | 20.7 | 4.9 | 34.9 | 1.3 |
| XXI | 22.1 | 74.1 | 2.6 | 61.5 | 23.0 | 5.6 | 35.1 | 1.0 |
| XXII | 22.1 | 74.1 | 2.6 | 62.9 | 22.0 | 5.1 | 35.7 | 1.2 |
| XXIII | 22.1 | 63.9 | 13.3 | 60.5 | 18.0 | 7.2 | 32.7 | 1.8 |
| XXIV | 22.1 | 74.1 | 2.6 | 62.7 | 21.6 | 4.4 | 35.7 | 1.8 |

Reaction condition:
Temp. 400° C.; Press. 27.9 kg/cm$^2$, WHSV = 3 hr$^{-1}$; H2/HC molar ratio = 3

EXAMPLE XXV

After being impregnated with tin by use of an aqueous SnCl$_2$ solution, a hydrogen form of mordenite with a mole ratio of silica/alumina of 90 was molded, together with gamma alumina as a binder, into a cylindrical shape 2 mm in diameter and 10 mm in length, so as to give a tin-impregnated carrier in which the mordenite amounted to 50 wt % based on the total weight of the carrier consisting of the mordenite and the gamma alumina binder and the tin amounted to 0.4 weight parts based on 100 weight parts of the carrier. The tin-impregnated carrier was dried at 150° C. for 10 hours and then, calcined at 500° C. for 3 hours. The resulting tin-contained carrier was treated with an aqueous H$_2$PtCl$_6$ solution such that 0.04 weight parts of platinum were impregnated in 100 weight parts of the carrier consisting of the mordenite and the binder. Thereafter, the resulting carrier was dried at 150° C. for 10 hours and calcined at 500° C. for 3 hours to allow a catalyst. This was tested for the same disproportionation/ transalkylation as in Example I, but using the reactant mixture indicated in Table 5. The reaction conditions and results are given in Table 5.

EXAMPLE XXVI

A catalyst was prepared in the same manner as that of Example XXV, except for using a hydrogen form of beta zeolite with a mole ratio of silica/alumina of 25. The catalyst was tested for disproportionation/transalkylation as in Example XXV. The results are given as shown in Table 5.

EXAMPLE XXVII

After being impregnated with tin by use of an aqueous SnCl$_2$ solution, a hydrogen form of mordenite with a mole binder. Thereafter, the resulting carrier was dried at 150° C. for 10 hours and calcined at 500° C. for 3 hours to allow a catalyst. This was tested for the same disproportionation/transalkylation as in Example I, but using the reactant mixture indicated in Table 5. The reaction conditions and results are given in Table 5.

EXAMPLE XXVIII

A catalyst was prepared in the same manner as that of Example XXVII, except for using a hydrogen form of beta zeolite with a mole ratio of silica/alumina of 25. The catalyst was tested for disproportionation/transalkylation as in Example XXVII. The results are given as shown in Table 5.

EXAMPLE XXIX

A catalyst was prepared in the same manner as that of Example XXV, except that an aqueous Pb(NO$_3$)$_2$ solution, instead of an aqueous SnCl$_2$ solution, was used to impregnate 0.5 weight parts of lead in 100 weight parts of the carrier. The catalyst was tested for disproportionation/transalkylation as in Example XXV. The results are given as shown in Table 5.

EXAMPLE XXX

A catalyst was prepared in the same manner as that of Example XXVII, except that an aqueous Pb(NO$_3$)$_2$ solution, instead of an aqueous SnCl$_2$ solution, was used to impregnate 0.5 weight parts of lead in 100 weight parts of the carrier. The catalyst was tested for disproportionation/transalkylation as in Example XXVII. The results are given as shown in Table 5.

TABLE 5

Assay for Disproportionation/Transalkylation Performance

| Nos. of Exmpl. | Aromatic Reactants (wt %) | | | Aromatic Products (wt %) | | | Yield of mixed xylenes (wt %) | Aromatic Loss (wt %) |
|---|---|---|---|---|---|---|---|---|
| | C6–C8 | C9 | C10 | C6–C8 | C9 | C10 | | |
| XXV | 21.1 | 63.9 | 13.3 | 61.0 | 18.8 | 8.1 | 33.3 | 1.7 |
| XXVI | 21.1 | 63.9 | 13.3 | 60.1 | 19.0 | 8.5 | 32.2 | 1.2 |
| XXVII | 22.1 | 74.1 | 2.6 | 61.7 | 23.6 | 6.1 | 35.0 | 0.8 |
| XXVIII | 22.1 | 74.1 | 2.6 | 62.0 | 23.3 | 5.7 | 35.2 | 1.2 |
| XXIX | 21.1 | 63.9 | 13.3 | 61.9 | 18.3 | 7.7 | 32.9 | 1.9 |
| XXX | 22.1 | 74.1 | 2.6 | 62.3 | 22.4 | 4.7 | 35.6 | 1.4 |

Reaction condition:
Temp. 400° C.; Press. 27.9 kg/cm$^2$, WHSV = 3 hr$^{-1}$; H2/HC molar ratio = 3

EXAMPLE XXXI

A catalyst was prepared in a similar manner to that of Example I, except that a mixture of a hydrogen form of mordenite and a hydrogen form of beta zeolite which had mole ratios of silica/alumina of 90 and 25, respectively, was molded, together with gamma alumina as a binder, into a cylindrical shape 2 mm in diameter and 10 mm in length, so as to allow a carrier in which the mordenite, the beta zeolite and the gamma alumina amounted to 30 wt %, 25 wt % and 45 wt %, respectively. The catalyst was tested for disproportionation/transalkylation as in Example I. The results are given as shown in Table 6.

EXAMPLE XXXII

A catalyst was prepared in a similar manner to that of Example I, except that a mixture of a hydrogen form of mordenite, a hydrogen form of beta zeolite and a hydrogen form of ZSM-5 which had mole ratios of silica/alumina of 90, 25 and 80, respectively, was molded, together with gamma alumina as a binder, into a cylindrical shape 2 mm in diameter and 10 mm in length, so as to allow a carrier in which the mordenite, the beta zeolite, the ZSM-5 and the gamma alumina amounted to 20 wt %, 20 wt %, 15 wt % and 45 wt %, respectively. The catalyst was tested for disproportionation/transalkylation as in Example I, but using the reactant mixture indicated in Table 6. The results are given as shown in Table 6.

EXAMPLE XXXIII

A catalyst was prepared in the same manner as that of Example XXXI, except that an aqueous Pb(NO$_3$)$_2$ solution, instead of an aqueous SnCl$_2$ solution, was used to impregnate 0.5 weight parts of lead in 100 weight parts of the carrier. The catalyst was tested for disproportionation/transalkylation as in Example XXXI. The results are given as shown in Table 6.

EXAMPLE XXXIV

A catalyst was prepared in the same manner as that of Example XXXII, except that an aqueous Pb(NO$_3$)$_2$ solution, instead of an aqueous SnCl$_2$ solution, was used to impregnate 0.5 weight parts of lead in 100 weight parts of the carrier. The catalyst was tested for disproportionation/transalkylation as in Example XXXII. The results are given as shown in Table 6.

TABLE 6

Assay for Disproportionation/Transalkylation Performance

| Nos. of Exmpl. | Aromatic Reactants (wt %) | | | Aromatic Products (wt %) | | | Yield of mixed xylenes (wt %) | Aromatic Loss (wt %) |
|---|---|---|---|---|---|---|---|---|
| | C6–C8 | C9 | C10 | C6–C8 | C9 | C10 | | |
| XXXI | 65.5 | 31 | 2.9 | 79.5 | 13.0 | 3.7 | 32.7 | 1.2 |
| XXXII | 22.1 | 74.1 | 2.6 | 63.0 | 22.0 | 4.8 | 36.0 | 1.5 |
| XXXIII | 65.5 | 31 | 2.9 | 78.9 | 13.4 | 4.0 | 32.5 | 1.0 |
| XXXIV | 22.1 | 74.1 | 2.6 | 64.5 | 21.2 | 4.1 | 36.7 | 1.9 |

Reaction condition:
Temp. 400° C.; Press. 27.9 kg/cm$^2$, WHSV = 3 hr$^{-1}$; H2/HC molar ratio = 3

As described hereinbefore, the catalysts according to the present invention enable mixed xylenes to be produced at remarkably high yields from benzene, toluene and C9 or higher aromatic compounds through disproportionation/transalkylation with a great reduction in aromatic loss. In addition, the catalysts can maintain their catalytic activity for a long period of time without deactivation. Therefore, they can be usefully applied for industrial purposes.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A process for producing mixed xylenes from aromatic hydrocarbons, said process comprising:

(A) providing an aromatic hydrocarbon feedstock comprising:
  (1) toluene and
  (2) C9 or higher aromatic hydrocarbons;

(B) converting said aromatic hydrocarbons in said feedstock into mixed xylenes by contacting said feedstock with hydrogen in the presence of a catalyst, said catalyst comprising:
  (1) a carrier comprising:
    (a) 10 to 80 wt % of at least one of
      (i) mordenite and
      (ii) beta type zeolite,
  said mordenite and said beta type zeolite having a mole ratio of silica to alumina of from 10 to 200;
    (b) from greater than 0 up to 70 wt % of ZSM-5 type zeolite having a mole ratio of silica to alumina of from 30 to 500; and
    (c) 5 to 90 wt % of at least one inorganic binder selected from the group consisting of gamma-alumina, silica, silica-alumina, bentonite, kaolin, clinoptilolite and montmorillonite; and
  (2) a metal component, supported on said carrier, said metal component comprising:
    (a) platinum, and
    (b) either tin or lead; and (C) recovering said mixed xylenes.

2. The process of claim 1 wherein platinum is present in the carrier in an amount of from 0.001 to 0.5 wt. parts based on 100 weight parts of the carrier.

3. The process of claim 2 wherein tin is present in the carrier in an amount of from 0.01 to 10.0 weight parts based on 100 weight parts of the carrier.

4. The process of claim 3, wherein the metal component consists essentially of platinum and tin.

5. The process of claim 2 wherein lead is present in the carrier in an amount of from 0.01 to 7.0 weight parts based on 100 weight parts of the carrier.

6. The process of claim 5, wherein the metal component consists essentially of platinum and lead.

7. The process of claim 1 wherein said catalyst has been prepared by a process comprising the steps of:
  (1) forming a carrier which comprises
    (a) 10 to 80 wt % of at least one of
      (i) mordenite and
      (ii) beta type zeolite;
  said mordenite and said beta type zeolite having a mole ratio of silica to alumina from 10 to 200;
    (b) from greater than 0 up to 70 wt % of ZSM-5 type zeolite having a mole ratio of silica to alumina of from 30 to 500; and
    (c) 5 to 90% of at least one inorganic binder selected from the group consisting of gamma-alumina, silica, silica alumina, bentonite, kaolin, clinoptilolite and montmorillonite;
  (2) supporting 0.01 to 10.0 weight parts of tin or 0.01 to 7.0 weight parts of lead in 100 weight parts of said carrier; and
  (3) supporting 0.001 to 0.5 weight parts of platinum on said tin- or lead-supported carrier, based on 100 weight parts of said carrier, to yield said catalyst.

8. The process of claim 1 wherein said catalyst has been prepared by a process comprising the steps of:

(1) mixing:
  (a) 10 to 80 wt % of at least one of:
    (i) mordenite and
    (ii) beta type zeolite;
  said mordenite and said beta type zeolite having a mole ratio of silica to alumina of from 10 to 200;
  (b) from greater than 0 up to 70 wt % of ZSM-5 type zeolite having a mole ratio of silica to alumina of from 30 to 500;
  (c) 5 to 90 wt % of at least one inorganic binder selected from the group consisting of gamma-alumina, silica, silica alumina, bentonite, kaolin, clinoptilolite and montmorillonite;
  (d) 0.01 to 10.0 weight parts of tin or 0.01 to 7.0 weight parts of lead in 100 weight parts of the carrier; and
  (e) 0.001 to 0.5 weight parts of platinum in 100 weight parts of the carrier on a tin or lead supported carrier; and
(2) molding the mixture to yield said catalyst.

9. The process of claim 1 wherein said catalyst has been prepared by a process comprising the steps of:
  (1) supporting 0.001 to 0.5 weight parts of platinum, based on 100 weight parts of said carrier, on at least one of:
    (i) mordenite and
    (ii) beta type zeolite;
  said mordenite and said beta type zeolite having a mole ratio of silica to alumina from 10 to 200;
  through impregnation or ion exchange;
  (2) molding said platinum, supported on at least one of:
    (i) mordenite and
    (ii) beta type zeolite; with
    (i) ZSM-5 type zeolite having a mole ratio of silica to alumina of from 30 to 500, and
    (ii) at least one inorganic binder selected from the group consisting of gamma alumina, silica, silica alumina, bentonite, kaolin, clinoptilolite and montmorillonite, into a certain form;
  wherein
    the at least one of: (i) mordenite and (ii) beta type zeolite;
    the ZSM-5 type zeolite; and
    the inorganic binder;
  are present in an amount of 10 to 80 wt %, from greater than 0 up to 70 wt %, and 5 to 90 wt %, respectively; and
  (3) supporting tin or lead in said molded form at an amount of 0.01 to 10.0 weight parts or 0.01 to 7.0 weight parts, respectively, based on 100 weight parts of the carrier, to yield said catalyst.

10. The process of claim 1 wherein said catalyst has been prepared by a process comprising the steps of:
  (1) supporting from 0.001 to 0.5 weight parts of platinum based on 100 weight parts of said carrier on a mixture of:
    (a) 10 to 80 wt % of at least one of
      (i) mordenite and
      (ii) beta type zeolite in a mole ratio of silica to alumina from 10 to 200;
  said mordenite and said beta type zeolite having a mole ratio of silica to alumina from 10 to 200; and
    (b) from greater than 0 up to 70 wt % of ZSM-5 zeolite in a mole ratio of silica to alumina of from 30 to 500;
  through impregnation or ion exchange;
  (2) molding the platinum-supported zeolite together with 5 to 90 wt % of at least one inorganic binder selected from the group consisting of gamma-alumina, silica, silica alumina, bentonite, kaolin, clinoptilolite and montmorillonite, into a certain form; and (3) supporting tin or lead in said molded form at an amount of 0.01 to 10.0 weight parts and 0.01 to 7.0 weight parts, respectively, based on 100 weight parts of the carrier, to yield said catalyst.

11. The process of claim 1 wherein said catalyst has been prepared by a process comprising the steps of:
  (1) supporting 0.01 to 10.0 weight parts of tin or 0.01 to 7.0 weight parts of lead, based on 100 weight parts of said carrier, on at least one of
    (i) mordenite and
    (ii) beta type zeolite;
  said mordenite and said beta type zeolite having a mole ratio of silica to alumina from 10 to 200;
  through impregnation or ion exchange;
  (2) molding the at least one of
    (i) tin- or lead-supported mordenite; and
    (ii) tin- or lead-supported beta type zeolite; with
    (i) ZSM-5 zeolite having a mole ratio of silica to alumina from 30 to 500; and
    (ii) at least one inorganic binder selected from the group consisting of gamma-alumina, silica, silica alumina, bentonite, kaolin, clinoptilolite and montmorillonite, into a certain form;
  wherein:
    the at least one of (i) mordenite; and (ii) beta type zeolite;
    the ZSM-5 type zeolite; and
    the inorganic binder
  are present in an amount of 10 to 80 wt %, from greater than 0 up to 70 wt %, and 5 to 90 wt %, respectively; and
  (3) supporting 0.001 to 0.5 weight parts of platinum, based on 100 weight parts of the carrier, in said molded form, to yield said catalyst.

12. The process of claim 1 wherein said catalyst has been prepared by a process comprising the steps of:
  (1) supporting 0.01 to 10.0 weight parts of tin or 0.01 to 7.0 weight parts of lead, based on 100 weight parts of said carrier, on a mixture of
    (a) 10 to 80 wt % of at least one of
      (i) mordenite and
      (ii) beta type zeolite;
    said mordenite and said beta type zeolite having a mole ratio of silica to alumina of from 10 to 200; and
    (b) from greater than 0 up to 70 wt % of ZSM-5 zeolite having a mole ratio of silica to alumina of from 30 to 500, through impregnation or ion exchange;
  (2) molding the tin- or lead-supported zeolite together with from 5 to 90% of at least one inorganic binder selected from the group consisting of gamma-alumina, silica, silica alumina, bentonite, kaolin, clinoptilolite and montmorillonite, into a certain form; and
  (3) supporting platinum in said molded form at an amount of 0.001 to 0.5 weight parts, based on 100 weight parts of the carrier, to yield said catalyst.

13. The proces of claim 1 wherein the aromatic hydrocarbon feedstock further comprises benzene.

14. The process of claim 1 wherein said ZSM-5 zeolite havaing a mole ratio of silica to alumina of from 30 to 500 is present in the carrier in an amount of from 15 to 70 wt %.

* * * * *